United States Patent [19]
Kos

[11] Patent Number: 5,833,330
[45] Date of Patent: Nov. 10, 1998

[54] PERSONAL ORGANIZER AND MEDICAL HEALTH CARE DELIVERY FACILITATION DEVICE

[76] Inventor: Joy Y. Kos, 3216 102nd Ave., Kenosha, Wis. 53144

[21] Appl. No.: 998,096

[22] Filed: Dec. 24, 1997

[51] Int. Cl.$^6$ .................................................. A61B 19/02
[52] U.S. Cl. .......................... 312/209; 312/245; 312/230; 312/234; 312/184; 206/570
[58] Field of Search ..................................... 206/570, 214, 206/224, 371; 312/245, 230, 234, 183, 184, 209, 324

[56] References Cited

U.S. PATENT DOCUMENTS

| | | | |
|---|---|---|---|
| 149,488 | 4/1874 | Leary ....................................... | 312/245 |
| D. 330,115 | 10/1992 | O'Brien . | |
| D. 360,578 | 7/1995 | Dees . | |
| D. 362,748 | 10/1995 | Schildkraut . | |
| 2,845,319 | 7/1958 | Menkemeir .......................... | 312/234 X |
| 3,421,347 | 1/1969 | Sotory . | |
| 3,521,936 | 7/1970 | Coker, Jr. ............................. | 312/245 X |
| 3,659,355 | 5/1972 | Aubin, Jr. ............................. | 312/230 X |
| 3,969,006 | 7/1976 | Brown .................................. | 312/209 X |
| 4,155,609 | 5/1979 | Skafte et al. ............................. | 312/245 |
| 4,209,212 | 6/1980 | McGoldrick ............................ | 312/245 |
| 4,324,446 | 4/1982 | LeSage ..................................... | 312/245 |
| 4,349,338 | 9/1982 | Heppler ............................... | 312/234 X |
| 4,718,524 | 1/1988 | Crumley . | |
| 4,763,791 | 8/1988 | Halverson et al. ...................... | 206/570 |
| 5,261,702 | 11/1993 | Mayfield . | |
| 5,427,231 | 6/1995 | Willimann . | |
| 5,431,450 | 7/1995 | Coleman . | |
| 5,598,923 | 2/1997 | Owens ................................. | 206/570 X |

FOREIGN PATENT DOCUMENTS

| | | | |
|---|---|---|---|
| 3012282 | 10/1981 | Germany ............................... | 312/230 |

*Primary Examiner*—Peter M. Cuomo
*Assistant Examiner*—Hanh V. Tran
*Attorney, Agent, or Firm*—John D. Gugliotta

[57] ABSTRACT

A personal organizer and medical health care delivery facilitation device is provided having a main body, which rests up against and is connected to a wall divided, while being divided into two rectangular interior panels. Attached to the front of the interior panels is a wipeable board used for acute medical instructions and a series of horizontally aligned personal object retaining pouches. The pouches are transparent and contain labeling indicia. A labeled space is provided for the names of family members and emergency phone numbers. Attached via hinges to the opposing ends of the interior panels are two exterior panels of equal size and shape to the interior panels. Attached to the front surface of each of the exterior panels is a written instruction retaining means, in a labeled, pouch like configuration, consisting of a transparent medium, such as plastic, and designed to hold papers such as written instructions from therapists and doctors and care cards. The two exterior panels close in cabinet like fashion.

4 Claims, 3 Drawing Sheets

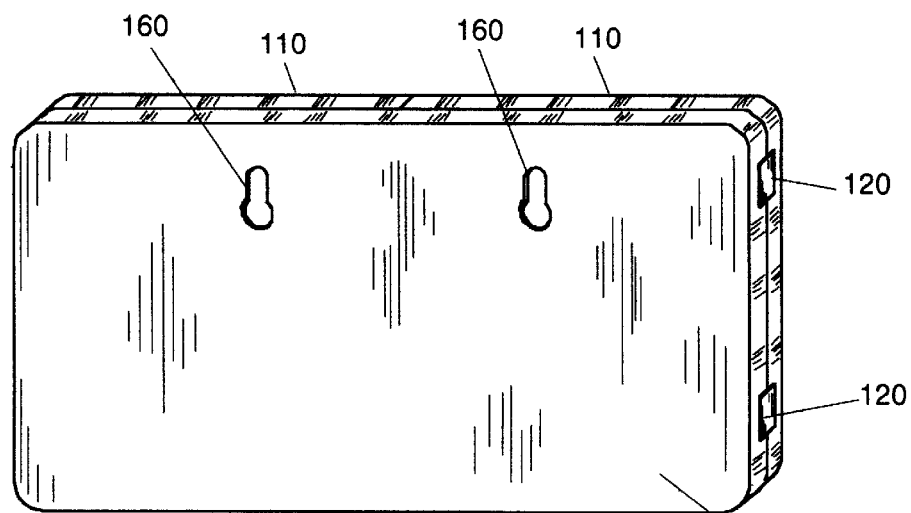
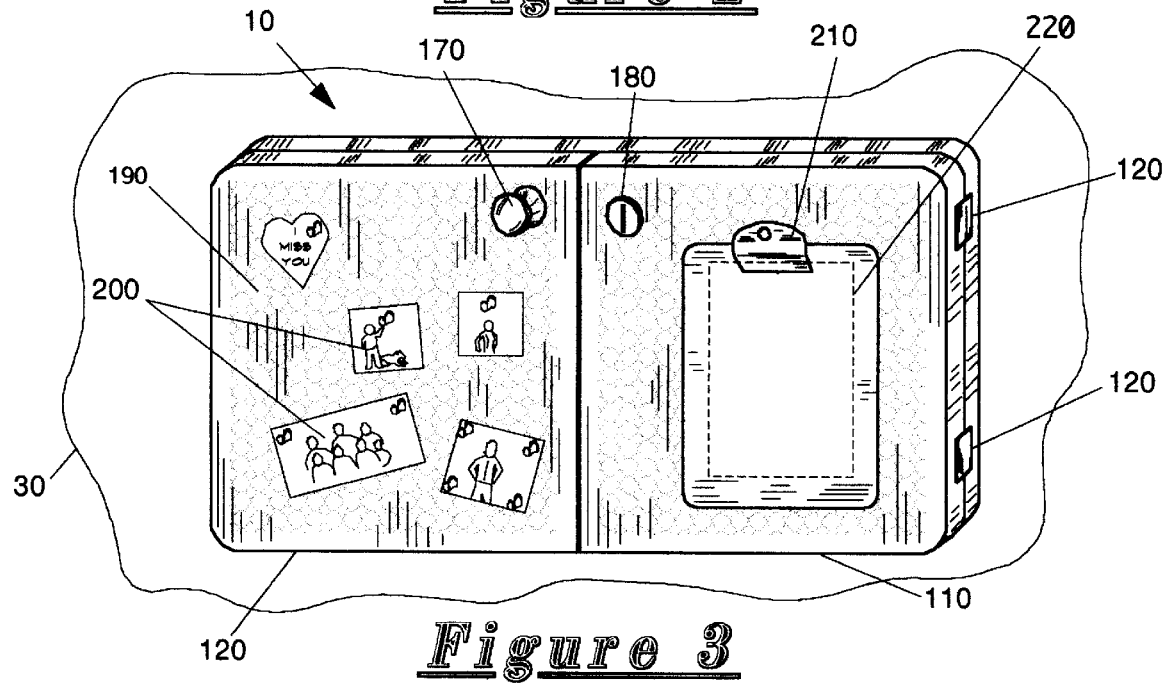

PERSONAL ORGANIZER AND MEDICAL HEALTH CARE DELIVERY FACILITATION DEVICE

BACKGROUND OF THE INVENTION

1. Field of the Invention

The present invention relates generally to personal organizers and, more particularly, to a personal organizer and medical health care delivery facilitation device.

2. Description of the Related Art

Patients in long term care facilities, such as nursing homes, have special needs and concerns. Because patients are often times invalids, they require that their personal items, such as combs, hearing aids, glasses, rosaries, watches, shavers, television viewing guides and remote controls, be positioned close to their bedsides. In addition, a major problem in long term care facilities is the disappearance and misplacement of such personal items. These items are traditionally kept everywhere in the patient's room, such as the closet, bedside stand drawer, on the bedside stand, in a drawer positioned across from the patient's bed, etc. In addition, there is a tendency for patients to take other patient's belongings from table tops and counter tops, the visiting patient mistaking the object for his or her own. All of these concerns necessitate that patients have their personal belongings in one easy to find and reach device, strategically placed so as to be out of the way to traffic in the facility, and away from the traditional places that such objects are typically kept, such as tables, etc. where they can be easily grabbed by mistake. Such a device cannot be institutional in its look, but rather must be aesthetically pleasing, in that the institutional feel is not desired in a long term care facility.

Care givers of long term care patients also have unique needs and constraints placed on them. Patient confidentiality of long term care patients is highly stressed and enforced in most long term care facilities. Currently, the care instructions for nursing assistants regarding each patient is taped inside the closet doors or in a closed chart hanging from the foot of the bed, or in a binder outside of the room. Instructions from the various therapy departments are placed in the same locations. These instructions are crucial to the proper care of the patients and must be easily seen and followed by the care givers. These instructions include how to apply various splints, how to do range of motion exercises, special speech therapy feeding instructions to avoid patient choking episodes, allergy warnings, and which side rail is to be up or down. Such instructions, if not followed, could lead to a patient being seriously injured or even killed.

The position of these instructions proves to be problematic to care givers. For example, nursing assistants must often put up a side rail and leave the patient momentarily to go across the room to read the instructions on how to continue care. It can be dangerous to leave patients in the middle of treatments. Also, the likelihood of mistakes is increased as the care giver must go back and forth between the patient and the care instructions.

In the related art, there are no devices that address all the various concerns associated with patient care and living in a long term care facility.

Most devices designed to assist patients in keeping their personal possessions, medicine, and other objects necessary for their rehabilitation in one place are designed to be kept on a tabletop or counter top.

Some devices, such as U.S. Design Patent No. D330,115, issued in the name of O'Brien, disclose personal organizers that keep paperwork relating to a patient in one place, such as a spiral binder. Devices exist for the holding of pills, such as U.S. Pat. No. 3,421,347, issued in the name of Sotory. Some devices are self-standing personal organizers, designed to hold objects such as glasses, pens, in its pockets. An example of this type of device is U.S. Pat. No. 4,718,524, issued in the name of Crumley.

There are several problems with these types of devices. First, the fact that they require counter or table space creates a problem when space is limited. These objects compete with objects like family pictures that are usually placed on counter and table tops. Second, these types of devices are likely to be knocked over by residents. Third, these devices are limited in that they are single purpose devices that meet only one of the patient's needs.

Some devices deal with the problems associated with limited counter space by placing a personal care device in a place other than a table. Some devices are designed to be hung in a closet, such as the device disclosed in U.S. Design Patent No. D362,748, issued in the name of Schildkraut. The '748 device discloses a organizer which hangs from a clothes hanger. This sort of device, while designed for use with sewing materials, could be used to store medicine and personal belongings.

The problem with this type of device is that it is stored away from where the patient and care giver normally are, thus requiring the care giver to leave the patient to get medicine from the closet and the patient to travel across the room to retrieve or return personal belongings to the device. During this time, the patient is at risk of injury from such events as falling out of bed. Also, the device is bulky and cumbersome to use.

The prior art contains several medication and care instruction systems which are secured to a wall. Examples of this type of device include U.S. Pat. No. 5,261,702, issued in the name of Mayfield, U.S. Pat. No. 5,431,450, issued in the name of Coleman, and U.S. Design Patent No. D360,578, issued in the name of Dees.

Such devices have several problems associated with their use. First, such devices do not provide the confidentiality required in nursing homes and other long term care facilities. Second, such devices do not address the other needs of patients discussed above.

Wall mounted organizers for personal accessories are represented in the prior art. For example, U.S. Pat. No. 5,427,231, issued in the name of Willimann, discloses a device containing numerous hooks to hold items such as brushes, shoe horns and scissors. The device, however, is limited in use, in that the objects being secured must be capable of being attached to the hooks. Also, the device is designed for household objects, such as scissors, and not for objects kept by a long term care patient, such as eye glasses, a television viewing guide, medicine, etc. Also, the device has no accommodations for patient care instructions or medical charts, as well as personal pictures. Furthermore, the device is bulky and projects outward from the wall significantly, increasing the chance patients would bump into it inadvertently if placed over their beds.

A search of the prior art did not disclose any patents that read directly on the claims of the instant invention. Consequently, a need has been felt for providing an apparatus and method which addresses all the needs mentioned above by blending in one device, the solution to the personal property storage needs of long term care patients and the need of health care providers for a device to simplify and facilitate the confidential delivery of safe, accurate health care.

SUMMARY OF THE INVENTION

It is therefore an object of the present invention to provide a personal organizer and medical health care delivery facilitation device that accommodates personal objects used by long term care patients, medicine, medical charts and all necessary care instructions, that is inexpensive, easy to manufacture and use, streamline in design, contains everything a care giver needs to care for the patient, can be placed in a position where it is readily available to the care giver as they are caring for the patient, such as wall mounted near the patient's bed, can be closed when not in use to protect the patients belongings from inadvertent loss or breakage, and is aesthetically pleasing.

Briefly described according to a preferred embodiment of the present invention, the present invention consists of a main body consisting of two interior panels, wipeable board with erasable pen and retaining means, personal object retaining means, labeling indicia, wall attachment means, exterior panels, panel securement means, written instruction retaining means, care cards, an operating knob, a lock and key assembly, and decorative material.

The main body rests up against and is connected to a wall, while being divided into two rectangular interior panels. Attached to the front of the interior panels is a wipeable board used for acute medical instructions and a series of horizontally aligned personal object retaining means, such as pouches. The pouches are transparent and contain labeling indicia. A labeled space is provided for the names of family members and emergency phone numbers.

Attached via hinges to the opposing ends of the interior panels are two exterior panels, of equal size and shape to the interior panels. Attached to the front surface of each of the exterior panels is a written instruction retaining means, in a labeled, pouch like configuration, consisting of a transparent medium, such as plastic, and designed to hold papers such as written instructions from therapists and doctors and care cards.

The two exterior panels close in cabinet like fashion, via a grasping means, to form a closed device, thereby providing patient confidentiality. A lock and key assembly is included to provide complete protection of personal items. The front of the device has attached to it a decorative material, such as fabric. The decorative surface is of sufficient thickness to allow objects, such as family pictures, to be connected to it via pins or other securement methods.

Attached to the front of the closed device is a paper securement means, where documents such as work schedules and the like can be easily attached, detached and viewed with the present invention still in the closed position.

It is another object of the present invention to provide a device that can hold the various items necessary to care for a particular patient, such as soap, tissues, bandages, etc.

It is another object of the present invention to provide a device that is wall mounted, thus allowing it to be positioned above a patient's bed for easy patient and care giver access.

It is another object of the present invention to provide see through written information retaining means, made from a transparent material such as plastic, that secure care cards and therapy instructions from the various therapists in an easy to find and read location. By eliminating hidden care giver instructions, greater assurance is given that care givers will follow all the instructions. Also, safety issues are readily visible, such that the incidents of patient choking and falls is greatly reduced. Continuity of care between care givers on different shifts is also facilitated, with all care givers providing the same care to the same patient.

It is another object of the present invention to provide a means that informs visiting family members of the type of care their loved one is receiving, and assures them that the long term care facility is doing everything possible to assure that the patient receives quality, continuous care. This peace of mind that is facilitated with the present invention should not be underestimated, as placing a loved one in a long term care facility can often times be stressful on other family members.

It is another object of the present invention to provide a personal object retaining means, that consists of pouches and can hold a variety of objects of differing size and configuration. This reduces the incidents of lost, misplaced or mistakenly taken personal items.

It is another object of the present invention to provide personal object retaining means that are see through and clearly labeled, thus making identification of items easier for the patients.

It is another object of the present invention to provide a wipeable board for acute instructions. This provides an easy way for health care professionals to communicate the patient's needs to workers on other shifts. Also, it enables quick changes in patient care instructions that will be seen by all care givers caring for a particular patient.

It is another object of the present invention to provide care cards, which list care instructions for each individual patient.

It is another object of the present invention to provide a device that can be closed, thus reducing the chance of object being lost or broken, while simultaneously ensuring patient confidentiality, as required in nursing homes and other long term care facilities.

It is another object of the present invention to provide a place for a list of family members names to be readily accessible to health care providers, thus facilitating the use of the family members' names to help calm and orient the patient.

It is another object of the present invention to provide a device that allows important object, such as family pictures, to be prominently displayed on the outside of the present invention. This feature helps the patient feel connected with their families and helps create a familiar atmosphere in what otherwise could be a difficult situation for them.

It is another object of the present invention to provide a place for family phone numbers, so that family members can be notified in case of an emergency.

It is another object of the present invention to provide a device that is aesthetically pleasing, adding to the decor and visual atmosphere of the rooms of long term care patients. Hospitals and nursing homes are now realizing that the color and texture of the walls and objects of a patient's room can affect their emotional state and attitudes regarding their environment and present situation, and consequently, their motivation and desire to remain active and healthy. The attractive outer covering of the present invention may help improve a patient's attitude.

Descriptive Key

- 10 personal organizer and medical health care delivery facilitation device
- 20 main body
- 30 wall
- 40 interior panel
- 50 wipeable board
- 60 erasable pen -continued Descriptive Key 70 wipeable board retaining means
80 personal object retaining means
90 personal objects
100 first labeling indicia
103 personal information section
105 family member names
107 emergency phone numbers
109 second labeling indicia
110 exterior panels
120 panel securement means
130 written instruction retaining means
140 written instructions
145 third labeling indicia
150 care cards
160 wall attachment means
170 operating knob
180 lock and key assembly
190 decorative material
200 family pictures
210 paper securement means
220 patient turning schedule

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 2 is a back view of the present invention;

FIG. 3 is a front perspective view of the present invention in the closed position;

DESCRIPTION OF THE PREFERRED EMBODIMENTS

In order to describe the complete relationship of the invention, it is essential that some description be given to the manner and practice of functional utility and description of a personal organizer and medical health care delivery facilitation device 10.

The best mode for carrying out the invention is presented in terms of its preferred embodiment, herein depicted within the FIGS. 1 through 5.

1. Detailed Description of the Figures

Figure 1:
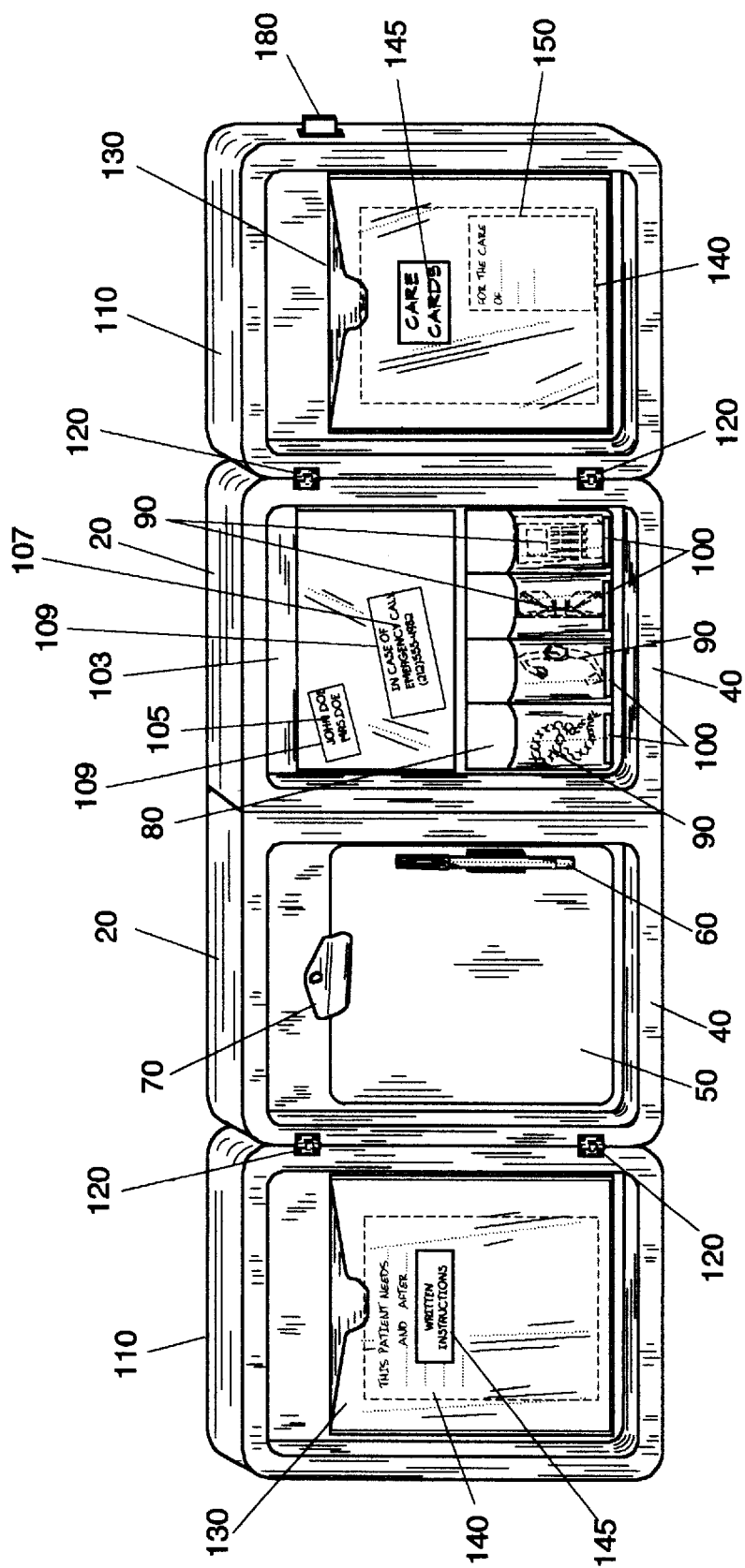
FIG. 1 is a front perspective view of a preferred embodiment of a personal organizer and medical health care delivery facilitation device 10 in the open position.

Referring now to FIG. 1, a personal organizer and medical health care delivery facilitation device 10 is shown, according to a preferred embodiment of the present invention, consisting of a main body 20. The main body 20 is laterally and vertically elongated and generally rectangular in shape, with its posterior surface being designed to rest flat against a wall 30. The main body 20 is divided into two interior panels 40 of equal size and whose anterior surfaces are of equal surface area.

Connected to the anterior surface of one of the interior panels 40 is a wipeable board 50, of generally rectangular configuration, and having an anterior surface that permits erasure of marks with a wet towel. An erasable pen 60 for use with the wipeable board 50 is detachably secured to the anterior surface of the wipeable board 50. A wipeable board retaining means 70 serves a dual function of connecting the wipeable board 50 to the anterior surface of one of the interior panels 40, and also permitting the wipeable board 50 to secure paper documents. The wipeable board retaining means 70 is a hinged, grasping mechanism, as is well known in the art. The wipeable board 50 is designed to allow for acute instructions from the primary physician or physicians.

Attached to the anterior surface of the remaining interior panel 40 are a series of personal object retaining means 80. The personal object retaining means 80 are a series of horizontally aligned pouches of equal height, constructed of a transparent material, such as plastic. The personal object retaining means 80 may be formed from one piece of material, or consist of separate units. Each personal object retaining means 80 may consist of two pieces of material connected together, or one piece of material connected along three sides to the interior panel 40.

Sufficient space is left at the top of each personal object retaining means 80 for a person to be able to reach into the personal object retaining means 80 and place or retrieve personal objects 90. Attached to the anterior surface of each personal object retainment means 80 is a first labeling indicia 100, which identifies where certain object are to be placed, such as eyeglasses, hearing aids, and the like.

Positioned on one of the interior panels 40 is a personal information section 103, where the patient can write family member names 105 and emergency phone numbers 107 second labeling indicia 109 are attached to the interior panel 40 to facilitate use of this area as heretofore designated, and being hidden when the present invention is in the closed position.

Attached to the opposing ends of the interior panels 40 are two exterior panels 110. Each exterior panel 110 is attached to its corresponding interior panel 40 by a panel securement means 120, such as a hinge.

Attached to the anterior surface of each of the exterior panels 110 is a written instruction retaining means 130, consisting of a transparent medium, such as plastic. Like the personal object retaining means 80, numerous configurations exist. For example, the written instruction retaining means 130 may be a single sheet of material connected on the bottom and sides to the exterior panel 110, or may consist of a pouch like configuration which itself is connected to the exterior panels 110. The written instruction retaining means 130 are of sufficient size to facilitate the insertion of written instructions 140 and other medical documents into them. Third labeling indicia 145, located on the anterior surface of the written instruction retaining means 130, inform care givers where to place certain medical information, such as therapy instructions and care cards 150. Care cards 150 are rectangular pieces of paper or card stock onto which specific care instructions are given for the primary care givers, such as nurses. The care cards 150 are designed to insert into one of the written instruction retaining means 130.

Referring now to FIG. 2, located on the posterior surface of the interior panels 40 are a wall attachment means 160. The wall attachment means 160 facilitates the attachment of the present invention to any vertical surface, such as a wall 30 or cabinet.

Referring now to FIG. 3, the two exterior panels 110 close in cabinet like fashion to form a closed, device, with each exterior panel 110 resting against the anterior surface of its adjacent interior panel 40 and the posterior surface of each exterior panel 110 becoming and forming the anterior surface of the device when closed.

Figure 5:
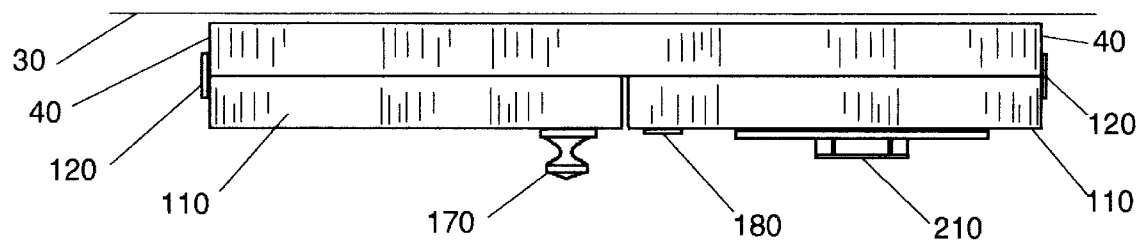
FIG. 5 is a top view.
Figure 4:
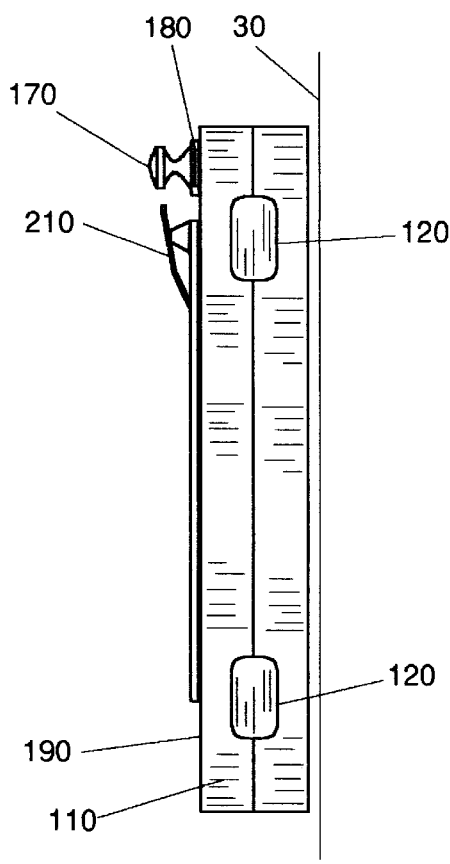
FIG. 4 is a right side view.

Referring now to FIGS. 3, 4 & 5, attached to the posterior surface of exterior panels 110 is an operating knob 170. The operating knob 170 is a graspable means for opening and closing the exterior panels 110. A cabinet style lock and key assembly 180 is positioned within the interior portion of one of the exterior panels 110 to provide security protection of valuables and confidentiality of medical information.

The anterior surface of the present invention when closed, which is formed by the posterior surface of the exterior panels 110, has attached to it a decorative material 190, such as fabric. The decorative material 190 is of sufficient thickness to allow objects, such as family pictures 200, to be connected to it via pins or other securement methods.

Attached to one of the exterior panels 110 that form the anterior surface of the closed present invention is a paper securement means 210, where documents such as the patient turning schedule 220 and the like can be easily attached, detached and viewed with the present invention still in the closed position. Thus, problems such as bedsores can be reduced significantly because the care givers know when the patient needs to be turned.

2. Operation of the Preferred Embodiment

To use the present invention, a care giver enters the patient's room, greets the resident and opens up the present invention. The care giver scans the written instructions 140 on the various panels and proceeds to care for the resident following the instructions of individualized care. If the patient is uncooperative or confused, the care giver uses the family names to reorient and reassure the resident. Following the therapy recommendations, the resident is encouraged to do as much for themselves as they can, thereby promoting their highest level of functioning. The care giver looks to see if assistance is needed transferring the patient out of bed. After the care is given, the care giver closes the present invention, and if appropriate, locks it. At bedtime, the residents place their personal objects 90 in the present invention. Other care givers who routinely check the patient will adhere to the patient turning schedule 220 should the patient require the same, thereby reducing the incidents of bedsores.

The foregoing description is included to illustrate the operation of the preferred embodiment and is not meant to limit the scope of the invention. The scope of the invention is to be limited only by the following claims.

What is claimed is:

1. A personal organizer and medical health care delivery facilitation device comprising:

a main body, said main body being generally rectangular in shape, and designed to rest against a vertical surface, and said main body further comprised of two interior panels of identical rectangular shape, each having an anterior surface and posterior surface;

a wall attachment means, said wall attachment means positioned on said posterior surface of said interior panels, and used to facilitate the connection of the personal and medical organizer to a vertical surface;

a wipeable board, having an anterior surface, said wipeable board being connected to said anterior surface of one of said interior panels, said wipeable board being of generally rectangular shape and having a surface that can be wiped clean after use with a wet paper towel;

an erasable pen, said erasable pen being secured to said wipeable board;

a wipeable board retaining means, said wipeable board retaining means used to secure said wipeable board to said anterior surface of said interior panel and securing paper documents to said anterior surface of said wipeable board, said wipeable board retaining means comprising a clasp shaped configuration secured to said anterior surface of said interior panel with rivets;

first labeling indicia, said first labeling indicia used to identify that acute care instructions are to be placed on said wipeable board;

personal object retaining means, said personal object retaining means comprising a horizontally aligned series of pouch like enclosure configurations of generally rectangular shape and equal height, composed of a transparent material such as plastic, and having an opening on the top and of such configuration such that a person can reach into and remove or place personal objects;

second labeling indicia, said second labeling indicia used to identify the particular personal object retaining means into which a particular said personal object is to be placed;

a personal information section, located on the anterior surface of one of said interior panels, for placement of family member names and emergency phone numbers;

third labeling indicia for indicating the location for placement of said family member names and said emergency numbers;

two exterior panels, said exterior panels having an anterior surface and posterior surface, and said exterior panels attached to opposing ends of said interior panels, forming a cabinet type configuration, said exterior panels being of identical size and configuration as said interior panels, and closing like cabinet doors against the said anterior surfaces of the corresponding said interior panels;

panel securement means, said panel securement means being of a hinge type configuration, and used to attach said each exterior panel to the adjacent one of said interior panel;

written instruction retaining means, said written instruction retaining means being of a pouch like configuration attached to each of said anterior surfaces of said exterior panels, and being of generally rectangular shape of sufficient size to facilitate the insertion of written instructions and other medical documents;

fourth labeling indicia, said fourth labeling indicia used to identify the written instruction retaining means and specific instructions such as therapist instructions;

care cards, said care cards being rectangular in shape and made of card stock onto which specific hygiene and care instructions are given for the primary care givers;

fifth labeling indicia indicating the placement of said care cards in said written instruction retaining means;

an operating knob, said operating knob being a grasping means located on said posterior surface of said exterior panels, said operating knob used to open and close said exterior panels;

a lock and key assembly, said lock and key assembly located inside of one of said exterior panels;

a decorative material, said decorative material attached to said posterior surface of both said exterior panels, with said decorative material being of sufficient thickness to facilitate attachment of family photographs via pins; and paper securement means, having an anterior surface, said paper securement means being located on said posterior surface of one of said exterior panels, said paper securement means being of rectangular configuration with a clamp type appendage projecting from the anterior surface of said paper securement means, and said paper securement means connected to the posterior surface of one of said exterior panels via rivets.

2. The personal and medical organizer described in claim 1, wherein said personal object retaining means further comprises a single sheet of transparent material connected on the bottom and sides and connected in vertical lines so as to form several pockets.

3. The personal and medical organizer described in claim 1, wherein said personal object retaining means further comprises a plurality of separate pouch like enclosures that are each individually connected to said anterior surface of said interior panel.

4. The personal and medical organizer described in claim 1, wherein said written instruction retaining means consist of a single sheet of transparent material attached along the bottom surface and sides to the anterior surface of the exterior panels so as to form a pouch like configuration, thus allowing a person to reach into said written instruction retaining means and remove said written instructions.

* * * * *